United States Patent [19]

Uphues et al.

[11] Patent Number: 5,962,709
[45] Date of Patent: Oct. 5, 1999

[54] PROCESS FOR THE AFTERTREATMENT OF BETAINES AND AMPHOTERIC SURFACTANTS

[75] Inventors: Günter Uphues, Monheim; Uwe Ploog, Haan; Rainer Jeschke, Düsseldorf; Renate Schick, Haan, all of Germany

[73] Assignee: Henkel Kommanditgesellschaft auf Aktien (KGaA), Duesseldorf, Germany

[21] Appl. No.: 08/525,693

[22] PCT Filed: Mar. 3, 1994

[86] PCT No.: PCT/EP94/00621

§ 371 Date: Sep. 12, 1995

§ 102(e) Date: Sep. 12, 1995

[87] PCT Pub. No.: WO94/20452

PCT Pub. Date: Sep. 15, 1994

[30] Foreign Application Priority Data

Mar. 12, 1993 [DE] Germany .................. P 43 07 791

[51] Int. Cl.$^6$ .................................. C07C 231/00
[52] U.S. Cl. ................ 554/70; 564/281; 564/291; 564/296; 252/541; 252/544; 252/547
[58] Field of Search .................. 524/281, 291, 524/296; 884/70; 252/541, 544, 547

[56] References Cited

U.S. PATENT DOCUMENTS 3,072,690  1/1963  Lee et al. .................. 260/404.5
5,281,749  1/1994  Uphues ............................ 562/40
5,292,942  3/1994  Aigner et al. ..................... 562/575

FOREIGN PATENT DOCUMENTS 0020907  1/1981  European Pat. Off. .
2063424  7/1972  Germany .
2926479  11/1980  Germany .
3939264  5/1991  Germany .
4035722  5/1992  Germany .
0771082  3/1957  United Kingdom .
9108193  6/1991  WIPO .

OTHER PUBLICATIONS

Parf. Cosm. Arom. 70, 67 (1986).

Happi, 70, (Nov. 1986).

Soap Cosm. Chem. Spec. 46, (Apr. 1990).

*Primary Examiner*—Gary Geist
*Assistant Examiner*—Deborah D Carr
*Attorney, Agent, or Firm*—Ernest G. Szoke; Wayne C. Jaeschke; Henry E. Millson, Jr.

[57] ABSTRACT

Process for the aftertreatment of betaine and amphoteric surfactants comprising adjusting the pH to the range of from 11 to 14 by addition of an alkali metal hydroxide, followed by a thermal aftertreatment if the surfactant contains dichloroacetic acid residues.

20 Claims, No Drawings

PROCESS FOR THE AFTERTREATMENT OF BETAINES AND AMPHOTERIC SURFACTANTS

This application is a 371 of PCT/EP94/00621 filed Mar. 3, 1994.

BACKGROUND OF THE INVENTION

1. Field of the Invention

This invention relates to a process for the aftertreatment of betaines and amphoteric surfactants in which the surfactants are alkalized and subjected to a thermal aftertreatment.

2. Statement of Related Art

Betaines and amphoteric surfactants show high compatibility with the skin and exhibit excellent cleaning properties. Accordingly, they are particularly suitable for the production of a number of surface-active products. In the most simple case, they are produced from tertiary amines which are reacted with sodium chloroacetate to form alkyl betaines. The reaction of fatty acid amidoamines or imidazolines with sodium chloroacetate leads to the formation of amphoteric surfactants of the glycinate type. If acrylates are used as the alkylating agent, aminopropionates are formed. Compounds of the type mentioned are described in a number of synoptic articles of which it is only intended here to cite Parf. Cosm. Arom. 70, 67 (1986), HAPPI, 70, (November 1986) and Soap Cosm. Chem. Spec. 46, (April 1990).

A particular concern in the production of betaines and amphoteric surfactants is to provide pure and hence dermatologically and toxicologically safe products. For example, traces of chloroacetic acid and, more particularly dichloroacetic acid, in the surfactants are undesirable. Preservatives which are intended to protect the betaines and amphoteric surfactants against microbial contamination are also frequently undesirable, so that there is a further need for products which are stabilized against microbial contamination even without the addition of auxiliaries. Finally, a third problem addressed by the present invention was to provide light-colored products.

A number of publications offering partial solutions to the cumulated problem are known from the prior art.

For example, it is proposed in DE-A1 39 39 264 (Henkel) to reduce the content of chloroacetic acid in amphoteric surfactants by subsequent treatment of the aqueous solutions with ammonia, amino acids or oligopeptides. DE-OS 29 26 479 (Th. Goldschmidt) describes a process in which the quaternization is carried out at a pH value of 7.5 to 10.5 and the residual content of free alkylating agent is thus reduced. The teaching of DE-A 20 63 424 (Rewo), which describes pH adjustment for the alkylation of imidazolines, points in the same direction. However, these processes do not have any influence on the content of dichloroacetic acid.

Sodium hypochlorite and, more particularly, hydrogen peroxide are used to bleach surface-active compounds. Bleaching is generally carried out in a neutral or acidic medium because $H_2O_2$ quickly decomposes under alkaline conditions. However, the acidic peroxide bleaching of betaines and amphoteric surfactants often produces only a temporary lightening of color, the color darkening again after storage.

In addition, a process for the preservative-free stabilization of special nonionic surfactants, so called alkyl polyglucosides, in which the aqueous solutions are adjusted to a pH value of at least 7, is known from the literature (DE-A1 40 35 722, Henkel). However, in view of the differences in structure between the nonionic alkyl polyglucosides and the betaines or amphoteric surfactants, which in addition also contain a hydrolyzable amide bond, application of the process to betaines and amphoteric surfactants appears to offer little promise.

DESCRIPTION OF THE INVENTION

The present invention relates to a process for the aftertreatment of betaines and amphoteric surfactants, in which the surfactants are adjusted to a pH value of 11 to 14 and preferably 12 to 13.5 by addition of alkali metal hydroxides and are subjected to a thermal aftertreatment, optionally under elevated pressure.

It has surprisingly been found that the thermal aftertreatment of betaine surfactants in a highly alkaline medium leads to a rapid and substantially quantitative reduction in the content of dichloroacetic acid. This was all the more surprising insofar as even betaines containing an amide bond proved to be extremely resistant to hydrolysis under these highly alkaline conditions and no significant change in the acid or amine value could be observed, even in the event of prolonged storage. The invention includes the observation that the alkalized and aftertreated products are excellently stabilized against microbial contamination so that there is no longer any need for additional preservation. Finally, it was surprisingly found that the highly alkalized products obtained by the process according to the invention are readily accessible to peroxide bleaching so that, unexpectedly, light-colored products can be obtained.

Betaines and amphoteric surfactants

Basically, the process according to the invention may be applied to any betaines and amphoteric surfactants. Although the advantage of removing dichloroacetic acid does not of course apply to those types that are not produced by alkalization with sodium chloroacetate, for example aminopropionates or sulfobetaines, the thermal aftertreatment of the highly alkalized products stabilizes the surfactants against microbial contamination even in these cases and makes the surfactants more accessible to peroxide bleaching.

However, the process according to the invention may be applied with advantage to betaines of the alkyl betaine type which correspond to formula (I):

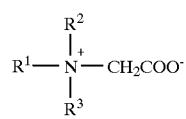

(I)

in which $R^1$ is an alkyl and/or alkenyl radical containing 6 to 22 carbon atoms and $R^2$ and $R^3$ independently of one another represent an alkyl and/or hydroxyalkyl radical containing 1 to 4 carbon atoms.

Typical examples are reaction products of tertiary amines, more particularly dimethyl alkylamines, with sodium chloroacetate.

Another preferred group of starting materials are glycinates or fatty acid amide-N, N-dialkyl betaines corresponding to formula (II):

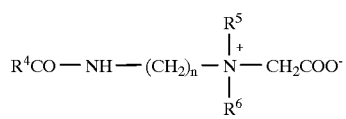

(II)

in which $R^4CO$ is a saturated and/or unsaturated acyl radical containing 6 to 22 carbon atoms, $R^5$ is hydrogen or an alkyl and/or hydroxyalkyl radical containing 1 to 4 carbon atoms, $R^6$ is an alkyl and/or hydroxyalkyl radical containing 1 to 4 carbon atoms and n=2 or 3. Betaines corresponding to formula (II), in which $R^4CO$ is an acyl radical containing 8 to 18 carbon atoms, $R^5$ and $R^6$ represent a methyl and/or hydroxyethyl group and n=3, are preferably used in the process according to the invention.

Thermal aftertreatment

A crucial precondition for the process according to the invention lies in the adjustment of the pH value. The pH value is normally adjusted by addition of an alkali metal hydroxide to the water-containing pastes or solutions of the betaines or amphoteric surfactants. The alkali metal hydroxides may be used in the form of 5 to 55% by weight aqueous solutions and preferably in the form of 25 to 50% by weight aqueous solutions. Concentrated sodium hydroxide solutions, i.e. approximately 50% by weight sodium hydroxide solutions, are preferably used.

The alkalized betaines or amphoteric surfactants are then subjected to a thermal aftertreatment. The aftertreatment may be carried out at temperatures of 20 to 130° C., for example in a stirred tank reactor. In one preferred embodiment of the process according to the invention, however, the aftertreatment is carried out in a pressure vessel at temperatures of 90 to 120° C., optionally under an elevated autogenous pressure of around 1 to 2 bar. The primary object of the thermal aftertreatment is to reduce the content of dichloroacetic acid which requires a reaction time of 0.1 to 5 h and preferably 1 to 3 h. At the same time, however, the content of any free monochloroacetic acid present is also significantly reduced, i.e. to below the instrument detection limit.

By contrast, if the objective is solely to achieve adequate stabilization against microbial contamination and to improve the bleachability of the surfactants, it is sufficient to adjust the products to a highly alkaline pH value at room temperature and immediately to further treat them, for example to bleach them by addition of 0.01 to 1% by weight and preferably 0.1 to 0.5% by weight of hydrogen peroxide, based on the solids content of the products, at temperatures in the range from 50 to 95° C. and preferably at temperatures in the range from 60 to 90° C.

After the thermal treatment, the products may, if desired, be adjusted to a pH value in the range from 7 to 5, for example by addition of mineral acid. If this measure is applied, the protection against microbial contamination is of course lost.

Commercial Applications

The products obtainable by the process according to the invention have an extremely low residual content of dichloroacetic acid and are stabilized against microbial contamination without any need for preservatives. Accordingly, they are suitable for the production of surface-active compositions, for example laundry detergents, dishwashing detergents and cleaning products and also hair care and body care products, in which they may be present in quantities of 1 to 30% by weight and preferably 2 to 10% by weight, based on the particular product.

The following Examples are intended to illustrate the invention without limiting it in any way.

EXAMPLES

I. Hydrolysis stability $C_{8/18}$ cocofatty acid amidopropyl-N,N-dimethylaminobetaine (Dehyton® K, a product of Henkel KGaA, Düsseldorf, FRG; solids content around 35% by weight) was adjusted to pH 11 by addition of aqueous sodium hydroxide solution and stored for 8 weeks at 20° C. and 40° C. During time, the pH value and the acid and amine values monitored. The results are set out in Table 1 below:

TABLE 1

Storage tests with Dehyton ® K

| | | pH value | | Acid value | | Amine value | |
|---|---|---|---|---|---|---|---|
| Ex. | t | 20° C. | 40° C. | 20° C. | 40° C. | 20° C. | 40° C. |
| 1 | 0 | 11.00 | 11.00 | 3.0 | 3.0 | 0.50 | 0.50 |
| 2 | 1 d | 10.89 | 11.31 | 2.7 | 3.1 | 0.47 | 0.53 |
| 3 | 3 d | 10.74 | 11.24 | 2.7 | 3.1 | 0.50 | 0.50 |
| 4 | 5 d | 10.66 | 11.24 | 2.6 | 2.9 | 0.50 | 0.50 |
| 5 | 2 w | 10.46 | 10.96 | 2.9 | 2.9 | 0.47 | 0.47 |
| 6 | 3 w | 10.42 | 10.92 | 2.9 | 2.8 | 0.47 | 0.50 |
| 7 | 4 w | 10.20 | 10.90 | 2.9 | 2.8 | 0.50 | 0.47 |
| 8 | 8 w | 10.20 | 10.88 | 2.9 | 3.0 | 0.50 | 0.53 |

Legend: t = Storage time

The Examples show that, even under extreme storage conditions (pH 11, 40° C., 8 weeks), the acid and amine values remain constant and no hydrolysis of the amide bond occurs.

II. Bleaching 0.1 to 1% by weight of hydrogen peroxide (30% by weight), based on the solids content, was added to $C_{8/18}$ cocofatty acid amidopropyl-N,N-dimethylaminobetaine (Dehyton® K, a product of Henkel KGaA, Düsseldorf, FRG; solids content approx. 35% by weight) at different pH values, followed by bleaching for 30 minutes at 60° C. The results are set out in Table 2 below:

TABLE 2

Bleaching of Dehyton ® K

| Ex. | pH value | $c(H_2O_2)$ % by weight | Color value APHA |
|---|---|---|---|
| 9 | 11 | 0.1 | 35 |
| 10 | 12 | 0.1 | 40 |
| 11 | 12 | 1.0 | 30 |
| 12 | 13 | 0.1 | 50 |
| C1 | 7 | — | 100 |
| C2 | 5 | 0.1 | 120 |
| C3 | 3 | 0.1 | 125 |
| C4 | 9 | 0.1 | 95 |

Legend: $c(H_2O_2)$ = Concentration of bleaching agent

III. Dichloroacetic acid content $C_{8/18}$ cocofatty acid amidopropyl-N,N-dimethylaminobetaine (Dehyton® K, a product of Henkel KGaA, Düsseldorf, FRG; solids content around 35% by weight) was adjusted to pH 12.5 to 13.5 by addition of aqueous sodium hydroxide solution (based on 10% by weight product solutions at 20° C.) and aftertreated in an autoclave for 0.5 to 3 h at a temperature of 90 to 120° C. and under a pressure of 1 to 1.1 bar. The results relating to the dichloroacetic acid content are set out in Table 3 below:

TABLE 3

Dichloroacetic acid content in Dehyton ® K

| Ex. | pH value | T °C. | p bar | t h | c(DCE) ppm | c(Alk) mmg |
|---|---|---|---|---|---|---|
| C3 | 7.0 | | | | 97 | 90.7 |
| C5 | 9.0 | 92 | 1.0 | 3.0 | 88 | 95.5 |
| C6 | 10.5 | 92 | 1.0 | 3.0 | 86 | 98.4 |
| 13 | 13.0 | 92 | 1.0 | 0.5 | 68 | 129.3 |
| | 13.0 | 92 | 1.0 | 1.0 | 61 | 129.3 |
| | 13.0 | 92 | 1.0 | 2.0 | 49 | 129.3 |
| | 13.0 | 92 | 1.0 | 3.0 | 38 | 129.3 |
| 14 | 13.5 | 92 | 1.0 | 0.5 | 62 | 132.9 |
| | 13.5 | 92 | 1.0 | 1.0 | 60 | 132.9 |
| | 13.5 | 92 | 1.0 | 2.0 | 46 | 132.9 |
| | 13.5 | 92 | 1.0 | 3.0 | 34 | 132.9 |
| 15 | 13.5 | 120 | 1.1 | 1.0 | 5 | 136.4 |
| | 13.5 | 120 | 1.1 | 2.0 | 5 | 136.4 |
| | 13.5 | 120 | 1.1 | 3.0 | 2 | 136.4 |
| 16 | 12.5 | 120 | 1.1 | 1.0 | 25 | 114.3 |
| | 12.5 | 120 | 1.1 | 2.0 | 5 | 114.3 |

Legend:
T = Aftertreatment temperature
t = Aftertreatment time
p = Pressure
c(DCE) = content of dichloroacetic acid (via HPLC)
c(Alk) = Total alkali content after titration with perchloroacetic acid
mmg = mmoles/100 g

We claim:

1. A process for reducing the content of dichloroacetic acid in a water-containing paste or solution of a betaine surfactant containing dichloroacetic acid residues wherein the betaine surfactant is at least one compound of the formula I or II

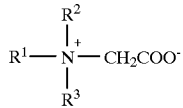
(I)

in which $R^1$ is an alkyl or alkenyl radical containing from 6 to about 22 carbon atoms, and $R^2$ and $R^3$ independently of one another represent an alkyl or hydroxyalkyl radical containing 1 to 4 carbon atoms,

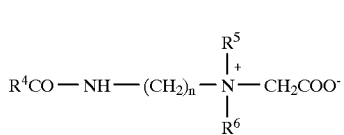
(II)

in which $R^4CO$ is a saturated or unsaturated acyl radical containing 6 to 22 carbon atoms, $R^5$ is hydrogen or an alkyl or hydroxyalkyl radical containing 1 to 4 carbon atoms, $R^5$ is an alkyl or hydroxyalkyl radical containing 1 to 4 carbon atoms, and n=2 or 3, comprising the steps of A) adding an alkali metal hydroxide to said paste or solution until a pH in the range of from about 11 to about 14 is obtained; and
B) thermally treating the resulting mixture until a significant reduction in residual dichloroacetic acid is achieved.

2. The process of claim 1 wherein step B) is carried out at a temperature in the range of from about 20 to 130° C.

3. The process of claim 2 wherein said temperature is in the range of from about 90 to about 120° C.

4. The process of claim 2 wherein step B) is carried out for a period of from about 0.1 to about 5 hours.

5. The process of claim 3 wherein step B) is carried out for a period of from about 1 to about 3 hours.

6. The process of claim 1 wherein in step A) the pH is in the range of from about 12 to about 13.5.

7. The process of claim 1 wherein step B) is carried out at a pressure of from 1 to about 2 bar.

8. The process of claim 1 wherein the paste or solution in step A) contains at least one alkyl betaine of the formula:

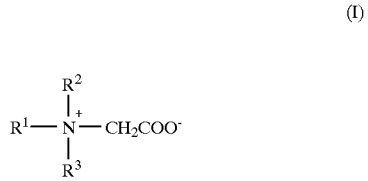
(I)

in which $R^1$ is an alkyl or alkenyl radical containing from 6 to about 22 carbon atoms, and $R^2$ and $R^3$ independently of one another represent an alkyl or hydroxyalkyl radical containing 1 to 4 carbon atoms.

9. The process of claim 1 wherein the paste or solution in step A) contains at least one compound of the formula

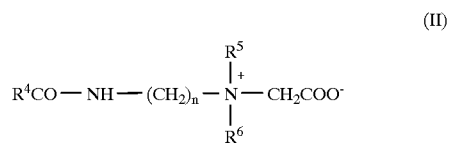
(II)

in which $R^4CO$ is a saturated or unsaturated acyl radical containing 6 to 22 carbon atoms, $R^5$ is hydrogen or an alkyl or hydroxyalkyl radical containing 1 to 4 carbon atoms, $R^5$ is an alkyl or hydroxyalkyl radical containing 1 to 4 carbon atoms, and n=2 or 3.

10. The process of claim 1 wherein in step A) the alkali metal hydroxide is sodium hydroxide.

11. The process of claim 1 wherein the mixture resulting from step B) is then bleached with hydrogen peroxide.

12. The process of claim 1 wherein the mixture resulting from step B) is adjusted to a pH in the range of from about 5 to about 7.

13. The process of claim 1 wherein the pH is in the range of from about 12 to about 13.5; and step B) is carried out at a temperature in the range of from about 90 to about 120° C.

14. The process of claim 13 wherein step B) is carried out for a period of from about 1 to about 3 hours under a pressure of from 1 to about 2 bar.

15. In a laundry detergent, dishwashing detergent, or cleaning composition, the improvement wherein from about 1 to about 30% by weight of the product of the process of claim 1 is added thereto.

16. The laundry detergent, dishwashing detergent, or cleaning composition of claim 15 wherein from about 2 to about 10% by weight of the product of the process of claim 1 is added thereto.

17. A process for stabilizing against microbial contamination a water-containing paste or solution of a betaine or amphoteric surfactant free from dichloroacetic acid residues comprising adding an alkali metal hydroxide to said paste or solution until a pH in the range of from about 11 to about 14 is obtained.

18. The process of claim 17 wherein said pH is in the range of from about 12 to about 13.5.

19. The process of claim 17 wherein the alkali metal hydroxide is sodium hydroxide.

20. The process of claim 17 wherein an additional step of bleaching with hydrogen peroxide is carried out on the paste or solution.

* * * * *